United States Patent [19]
Nierlich et al.

[11] Patent Number: 5,660,567
[45] Date of Patent: Aug. 26, 1997

[54] MEDICAL SENSOR CONNECTOR WITH REMOVABLE ENCODING DEVICE

[75] Inventors: Steve L. Nierlich; Phillip S. Palmer, both of San Leandro; Adnan I. Merchant, Fremont, all of Calif.

[73] Assignee: Nellcor Puritan Bennett Incorporated, Pleasanton, Calif.

[21] Appl. No.: 555,719

[22] Filed: Nov. 14, 1995

[51] Int. Cl.$^6$ .................................................. H01R 13/66
[52] U.S. Cl. ........................................ 439/620; 439/955
[58] Field of Search ................... 439/620, 488, 439/489, 490, 491, 607, 680, 189, 910, 950, 955

[56] References Cited

U.S. PATENT DOCUMENTS

| | | | |
|---|---|---|---|
| 3,790,910 | 2/1974 | McCormack | 235/151.3 |
| 3,910,701 | 10/1975 | Henderson et al. | 356/39 |
| 4,178,549 | 12/1979 | Ledenbach et al. | 325/38 R |
| 4,253,071 | 2/1981 | Underhill et al. | 332/9 T |
| 4,303,984 | 12/1981 | Houvig | 364/571 |
| 4,362,935 | 12/1982 | Clark, III | 378/48 |
| 4,418,392 | 11/1983 | Hata | 364/571 |
| 4,446,715 | 5/1984 | Bailey | 73/1 R |
| 4,621,643 | 11/1986 | New, Jr. et al. | 128/633 |
| 4,636,934 | 1/1987 | Schwendemann et al. | 364/132 |
| 4,684,245 | 8/1987 | Goldring | 356/41 |
| 4,695,815 | 9/1987 | Hwang | 439/910 |
| 4,700,708 | 10/1987 | New, Jr. et al. | 128/633 |
| 4,770,179 | 9/1988 | New, Jr. et al. | 128/633 |
| 4,858,615 | 8/1989 | Meinema | 128/668 |
| 4,897,854 | 1/1990 | Harris et al. | 375/17 |
| 4,900,261 | 2/1990 | Gentry et al. | 439/680 |
| 4,942,877 | 7/1990 | Sakai et al. | 128/633 |
| 5,078,136 | 1/1992 | Stone et al. | 128/633 |
| 5,202,682 | 4/1993 | Finger | 340/870 |
| 5,207,594 | 5/1993 | Olson | 439/490 |
| 5,244,409 | 9/1993 | Guss et al. | 439/490 |
| 5,405,269 | 4/1995 | Stupecky | 439/191 |

FOREIGN PATENT DOCUMENTS

| | | | |
|---|---|---|---|
| 2232016 | 11/1990 | United Kingdom | 439/910 |
| WO93/06776 | 4/1993 | WIPO | A61B 5/028 |

*Primary Examiner*—Neil Abrams
*Assistant Examiner*—T. C. Patel
*Attorney, Agent, or Firm*—Townsend and Townsend and Crew LLP

[57] ABSTRACT

A connector for a medical sensor is provided. The connector includes a number of contacts, and includes an electronic device for encoding a characteristic of the medical sensor. The electronic device is insertable into the connector. This simplifies the design of a sensor, which no longer needs to include a calibration element. In addition, the sensor can be made more cheaply, which is especially important for disposable sensors.

25 Claims, 1 Drawing Sheet

MEDICAL SENSOR CONNECTOR WITH REMOVABLE ENCODING DEVICE

BACKGROUND OF THE INVENTION

The present invention relates to medical sensors which include coded calibration information relating to characteristics of the sensor, and in particular to a connector for such a sensor.

An example of such an encoding mechanism is shown in U.S. Pat. No. 4,700,708. This relates to an optical oximeter probe which uses a pair of light emitting diodes (LEDs) to direct light through blood-perfused tissue, with a detector picking up light which has not been absorbed by oxygen in the blood. The operation depends upon knowing the wavelength of the LEDs. Since the wavelength of LEDs actually manufactured can vary, a resistor is placed in the sensor with the value of the resistor corresponding to the actual wavelength of at least one of the LEDs. When the instrument is turned on, it first applies a current to the coding resistor and measures the voltage to determine the value of the resistor and thus the value of the wavelength of the LED in the probe.

Another method of storing coded information regarding the characteristics of the LEDs is shown in U.S. Pat. No. 4,942,877. This patent discloses using an EPROM memory to store digital information, which can be provided in parallel or serially from the sensor probe to the remote oximeter.

Other examples of coding sensor characteristics exist in other areas. In U.S. Pat. No. 4,446,715, assigned to Camino Laboratories, Inc., a number of resistors are used to provide coded information regarding the characteristics of a pressure transducer. U.S. Pat. No. 3,790,910 discloses another pressure transducer with a ROM storing characteristics of the individual transducer. U.S. Pat. No. 4,303,984 shows another sensor with digital characterization information stored in a PROM, which is read serially using a shift register.

Typically, the coding element is mounted in the sensor itself. For instance, U.S. Pat. No. 4,621,643 shows the coding resistor mounted in the sensor element itself. In addition, U.S. Pat. No. 5,246,003 shows the coding resistor being formed with a printed conductive material on the sensor itself.

In some devices, an electrical connector coupled by a cable to a device attached to a patient may include a coding element. For example, U.S. Pat. No. 3,720,199 shows an intra-aortic balloon catheter with a connector between the catheter and the console. The connector includes a resistor with a value chosen to reflect the volumetric displacement of the particular balloon. U.S. Pat. No. 4,684,245 discloses a fiberoptic catheter with a module between the fiberoptic and electrical wires connected to a processor. The module converts the light signals into electrical signals, and includes a memory storing calibration signals so the module and catheter can be disconnected from the processor and used with a different processor without requiring a recalibration.

SUMMARY OF THE INVENTION

The present invention provides a connector for a medical sensor. The connector includes a number of contacts, and includes an electronic device for encoding a characteristic of the medical sensor. The electronic device is removably mounted in the connector. This simplifies the design of a sensor, which no longer needs to include a calibration element. In addition, the sensor can be made more cheaply, which is especially important for disposable sensors.

In one embodiment, the electronic device is a resistor enclosed in a clear plastic plug. The plug has two pins extending from it, and is inserted into a corresponding hole in the connector. When inserted, the pins are in alignment with the remaining pins of the connector to form the final connector configuration. The transparent plastic allows the resistor value to be observed and matched to a particular sensor during assembly. The plug is preferably inserted with a press-fit connection. The plug does not need to connect to anything else in a connector, since the signals for reading the resistor are provided from a remote oximeter monitor, and thus no signal needs to propagate beyond the connector to the sensor for performing this calibration.

In one embodiment, the connector includes a slot for engaging a corresponding tab on the oximeter monitor mating connector. This ensures that the proper type of sensor is only connected to the proper monitor. Additionally, or instead, a tab can be used to mate with a slot on the mating connector in the oximeter monitor.

For a further understanding of the nature and advantages of the invention, reference is made to the following description taken in conjunction with the accompanying drawings.

DESCRIPTION OF THE PREFERRED EMBODIMENTS

Figure 1:
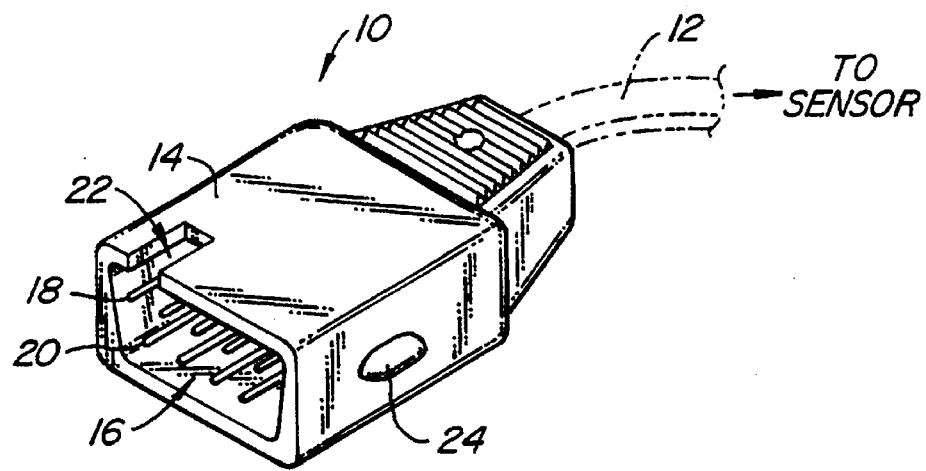
FIG. 1 is a perspective view of a connector according to the present invention.

FIG. 1 illustrates a connector 10 according to the present invention. A cable 12 connects to the remote sensor which is attached to the patient. The connector includes a casing 14 with an opening 16 in which a series of pins protrude. Included are pins 18 and 20 which connect to an electronic device encoding information regarding characteristics of the sensor attached to cable 12. The remaining pins provide connections to the sensor. For instance, in one embodiment, two pins or more will connect to two different LEDs in a pulse oximeter sensor. Another two pins will connect to a light detector in the oximeter sensor. Another pin connects to a shield. Other connections, such as for electrodes for monitoring other conditions, may be connected to pins of connector 10.

Connector 10 also includes a slot 22 adjacent pin 18, and a tab 24 along one side for aligning the connector and ensuring that it only connects to a proper mating connector, as described below with respect to FIG. 4.

Figure 2:
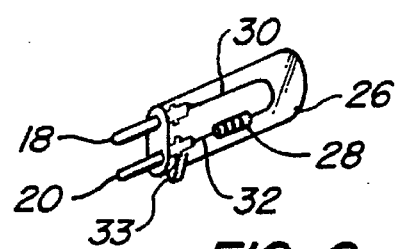
FIG. 2 is a diagram of a plug for insertion into the sensor of FIG. 1.

FIG. 2 illustrates a plug 26, preferably made of a clear plastic. Seen through the plug is an internal encoding resistor 28 connected by wires 30 and 32 to pins 18 and 20, respectively.

Figure 3:
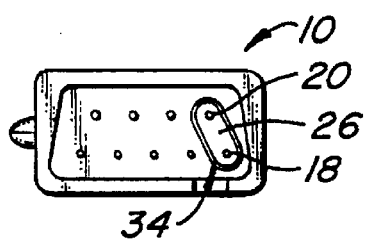
FIG. 3 is a diagram illustrating the plug of FIG. 2 inserted into the sensor connector of FIG. 1.

As shown in FIG. 3, plug 26 of FIG. 2 is inserted into a correspondingly-shaped hole 34 in connector 10. Preferably, the insertion is done with a press-fit. Alternatively, a locking tab 33 as is well-known in the art may be used to attach the plug 26 to connector 10.

During assembly, casing 14 is preferably formed around the pins (except 18 and 20) to form the connector body with hole 34. The connector is connected to cable 12, which is connected to a particular sensor. The wavelength of the red LED in the sensor attached to cable 12 is measured, and a resistor value indicating the wavelength spectrum of this/these LED(s) is selected. Preferably, a plurality of plugs 26 are on hand with varying resistor values. The resistor value can be observed since the plug 26 is made of clear plastic by viewing the color code on the side of the resistor. An appropriate plug is then selected, and inserted into hole 34 in connector 10 to provide a coding resistor corresponding to the particular LED value in the sensor connected to cable 12. Thus, as can be seen, the sensor need not include the coding resistor, and cable 12 need not include an additional two wires for connecting to a coding resistor in the sensor. This simplifies the sensor design, and allows it to be made more cheaply, an important factor for disposable sensors. In addition, the cable can be made smaller, and an additional source of potential electromagnetic interference is eliminated in the cable by eliminating the two wires which connect to the coding resistor.

In alternate embodiments, an active electronic device could be used in place of resistor 28. A memory could be used in place of resistor 28, or a modulating device for producing a modulation code corresponding to the LED wavelength could be used. Alternately, the connector could be used for sensors other than pulse oximeter sensors, for indicating other characteristics of the medical sensor. Instead of a plug 26, a detachable module which snaps into place or is otherwise connected to the connector could be used.

Figure 4:
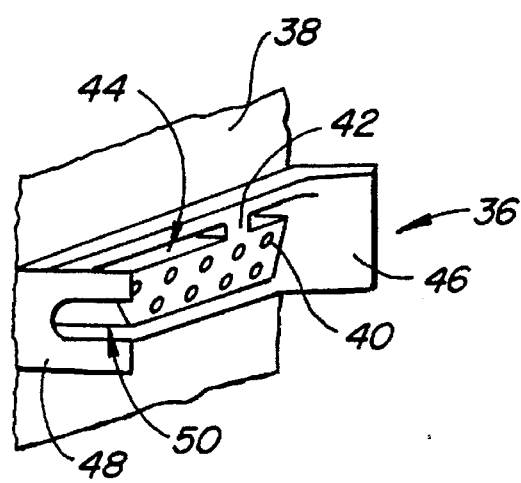
FIG. 4 is a perspective view of a mating connector on an oximeter monitor.

FIG. 4 illustrates a mating connector 36 mounted in an oximeter monitor 38, which is shown broken away. Connector 36 includes a plurality of female connector holes 40 for mating with the corresponding pins on connector 10. Also shown, is a tab 42, designed to mate with slot 22 of connector 10. Tab 42 interrupts a gap 44 which receives the outer edges of casing 14 of connector 10.

The mating connector 36 includes a pair of sidewalls 46 and 48, between which connector 10 would be inserted. Sidewall 48 includes a slot 50 for receiving tab 24 of connector 10. The use of tab 42 and slot 50, in conjunction with tab 24 and slot 22 in connector 10, ensures that the wrong type of sensor will not be connected to the oximeter monitor, or vice versa.

As will be understood by those of skill in the art, the present invention may be embodied in other specific forms without departing from the spirit and essential characteristics thereof. For example, only one of the slot and tab may be used to ensure proper connector mating, rather than both. Alternatively, the connector could have simply the slot, while the mating connector might have the tab in the slot, with the slot on the mating connector being superfluous. Additionally, a single pin might be connected to the resistor or other coding element of FIG. 2, with the plug having a connector for connecting to a separate pin internally to the connector, or simply connecting to a ground plane. Additionally, the notch and tab might be placed in different positions, with the different positions indicating the particular type of sensor to which the connector is attached. Alternatively, instead of press-fitting, the plug could be attached by gluing, welding and/or using a locking tab, etc. Accordingly, the above descriptions are intended to be illustrative, not limiting, of the scope of the invention, which is set forth in the appended claims.

We claim:

1. A connector for a medical sensor, comprising:
   a housing;
   a plurality of connector contacts disposed at least partially within a periphery of said housing; and
   an electronic device for encoding a characteristic of said medical sensor, removably mounted in said housing such that said electronic device may be inserted or removed without opening or disassembling said housing, and connected to at least one of said connector contacts before insertion into said housing.

2. The connector of claim 1 wherein said electronic device is a passive device.

3. The connector of claim 1 wherein said electronic device is a resistor.

4. The connector of claim 1 wherein said electronic device is an active device.

5. The connector of claim 1 further comprising a plurality of electrical wires for connecting said connector to said medical sensor.

6. The connector of claim 1 wherein said connector contacts comprise pins, and further comprising:
   a plug, insertable into said housing, holding said electronic device and having a pair of said pins extending therefrom; and
   an opening in said housing for receiving said plug.

7. The connector of claim 6 wherein said plug is glued into said opening in said housing.

8. The connector of claim 6 wherein said plug is welded into said opening in said housing.

9. The connector of claim 6 wherein said plug is held in said opening in said housing by a locking tab.

10. The connector of claim 6 wherein said plug is made of a plastic material which press-fits into said opening in said housing.

11. The connector of claim 10 wherein said plastic is transparent, allowing identification of said electronic device after encapsulation in said plastic and before insertion into said housing.

12. The connector of claim 1 further comprising a tab on said housing for mating with a corresponding slot in a mating connector.

13. The connector of claim 12 wherein said connector contacts comprise two rows of pins when said device is mounted in said housing, said tab being on a side of said housing adjacent to and at least partially between the levels of said two rows of pins.

14. The connector of claim 1 further comprising a slot on said housing for mating with a corresponding tab in a mating connector.

15. The connector of claim 14 wherein said connector contacts comprise two rows of pins when said electronic device is mounted in said housing, with four pins in a first row and five pins in a second row, said slot being adjacent an end pin in said second row.

16. A connector for an oximeter sensor, comprising:
    a housing;
    a plurality of connector contacts at least partially contained in said housing;
    an electronic device for encoding information corresponding to a wavelength spectrum of a light emitting diode in said oximeter sensor;
    a plug, separable from said housing, holding said electronic device and having a pair of device contacts, similar in shape to said connector contacts, extending therefrom; and an opening in said housing for receiving said plug such that said connector contacts and said device contacts are substantially parallel when said plug is inserted into said housing.

17. The connector of claim 16 wherein said electronic device is a resistor.

18. The connector of claim 16 wherein said electronic device an active device.

19. The connector of claim 16 further comprising a tab on said housing for mating with a corresponding slot in a mating connector.

20. The connector of claim 19 wherein said connector and device contacts comprise two rows of pins when said plug is mounted in said housing, said tab being on a side of said housing adjacent to and at least partially between the levels of said two rows of pins.

21. The connector of claim 16 further comprising a slot on said housing for mating with a corresponding tab in a mating connector.

22. The connector of claim 21 wherein said connector and device contacts comprise two rows of pins when said plug is mounted in said housing, with four pins in a first row and five pins in a second row, said slot being adjacent an end pin in said second row.

23. A method for constructing a connector for a medical sensor, comprising the steps of:

providing a connector body with a plurality of first contacts;

connecting an electronic device to at least one second contact, said electronic device encoding a characteristic of said medical sensor;

enclosing said electronic device in a plug;

inserting said plug into an opening in said connector body such that said first contacts and said at least one second contact are substantially parallel.

24. The method of claim 23 wherein said first and second contacts comprise pins, and further comprising the step of:

press-fitting said plug into said opening.

25. The method of claim 23 further comprising the step of forming said plug with a plastic material.

* * * * *